US00PP25431P3

(12) United States Plant Patent
Kapiteijn

(10) Patent No.: US PP25,431 P3
(45) Date of Patent: Apr. 7, 2015

(54) ***ZANTEDESCHIA* PLANT NAMED 'CAPTAIN ODEON'**

(50) Latin Name: *Zantedeschia sprengeri*
Varietal Denomination: CAPTAIN ODEON

(71) Applicant: Antonius Simon Johannes Kapiteijn, Anna Palowna (NL)

(72) Inventor: Antonius Simon Johannes Kapiteijn, Anna Palowna (NL)

(73) Assignee: Kapiteyn Breeding B.V. (NL)

( * ) Notice: Subject to any disclaimer, the term of this patent is extended or adjusted under 35 U.S.C. 154(b) by 166 days.

(21) Appl. No.: 13/815,779

(22) Filed: Mar. 14, 2013

(65) Prior Publication Data

US 2014/0283271 P1 Sep. 18, 2014

(30) Foreign Application Priority Data

Jul. 23, 2012 (QZ) ..... PBR 20121630

(51) Int. Cl.
*A01H 5/00* (2006.01)

(52) U.S. Cl.
USPC ..... Plt./490

(58) Field of Classification Search
USPC ..... Plt./490
See application file for complete search history.

*Primary Examiner* — Susan McCormick Ewoldt

(57) ABSTRACT

A new and distinct *Zantedeschia* cultivar named 'CAPTAIN ODEON' is disclosed, characterized by dark orange flowers, prolific flower production, green foliage spotted with white and a short plant height. The new variety is commercially suitable for indoor plant production.

1 Drawing Sheet

Latin name of the genus and species: *Zantedeschia sprengeri.*

Variety denomination: 'CAPTAIN ODEON'.

BACKGROUND OF THE INVENTION

This application claims priority benefit to European Union Plant Breeder's Rights application number 2012/1630 filed Jul. 23, 2012. The new cultivar is a product of a planned breeding program. The new variety originated from a cross pollination, made by the inventor in 2006, of a proprietary seed parent identified as '3434.34' and a proprietary pollen parent identified as '04.877-1', both *Zantedeschia sprengeri.*

The new variety was discovered and selected by the inventor, Anthonius Simon Johannes Kapiteijn, a citizen of the Netherlands, in 2008 in a group of seedlings resulting from the crossing. The new cultivar was found in a commercial greenhouse belonging to the inventor in Anna Paulowna, the Netherlands.

Asexual reproduction of the new cultivar 'CAPTAIN ODEON' was first performed by micropropagation at a commercial laboratory in Anna Palowna in the Netherlands in late 2009 or early 2010. Micropropagated plants were subsequently grown out to produce tubers. 'CAPTAIN ODEON' has been reproduced by both micropropagation and tubers and has shown that the unique features of this cultivar are stable and reproduced true to type.

SUMMARY OF THE INVENTION

The cultivar 'CAPTAIN ODEON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAPTAIN ODEON.' These characteristics in combination distinguish 'CAPTAIN ODEON' as a new and distinct *Zantedeschia* cultivar:

1. Deep orange flowers.
2. Prolific flower production.
3. Short plant height.
4. Green foliage with white spots.

PARENT COMPARISON

Plants of the new cultivar 'CAPTAIN ODEON' are similar to plants of the seed parent variety, in most horticultural characteristics, however, plants of the new cultivar produce spathes which are orange, whereas the seed parent produces pink spathes.

Plants of the new cultivar 'CAPTAIN ODEON' are similar to plants of the pollen parent variety, in most horticultural characteristics, however, plants of the new cultivar produce orange spathes whereas the spathes of the pollen parent are red. Additionally, typical peduncle length of the new variety is shorter than typical peduncle length of the pollen parent.

COMMERCIAL COMPARISON

Plants of the new cultivar 'CAPTAIN ODEON' are similar to plants of the unpatented variety, *Zantedeschia sprengeri* 'Captain Fuego', unpatented in most horticultural characteristics, however, plants of the new cultivar have a different leaf shape than 'Captain Fuego'. Additionally, 'Captain Odeon' produces flowers and foliage of deeper coloration than 'Captain Fuego'.

BRIEF DESCRIPTION OF THE PHOTOGRAPH

The accompanying photograph in FIG. 1 illustrates in full color typical plants of 'CAPTAIN ODEON' grown in a greenhouse in Anna Paulowna, the Netherlands. The plants are approximately 1 year old, shown growing in 15 cm pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CAPTAIN ODEON' plants grown in a climate controlled greenhouse in Anna Paulowna, the Netherlands. Temperatures ranged from 18° C. to 22° C. day to 12° C. to 16° C. at night. The following chemical treatments were used; GA 3 growth regulator at an unspecified amount during production. Before planting growth retardant, padobutrazol at a dose of 1 ppm was given. Measurements and numerical values represent averages of typical plant types.

Botanical classification: *Zantedeschia sprengeri* cultivar 'CAPTAIN ODEON'.

PROPAGATION

Time to initiate roots: About 10 days at approximately 18-22° C.

Typical propagation material: Plants for commercial flowering potted plant production are typically produced by planting a 2 year old tuber.

Root description: Moderately dense, moderately branched, slightly fibrous, non-fleshy colored white; near RHS NN155C.

Time to produce rooted plantlet: Approximately 10-30 days at approximately 18 to 22° C.

PLANT

Growth habit: Narrow upright, clumping, shoots grow directly from base.

Plant shape: Obovate.

Height: Approximately 36.6 cm to top of highest leaf. Approximately 40.5 cm to top of highest inflorescence.

Plant spread: Average: 30.0 cm.

Normal pot size: 14 cm circular pots and larger.

Growth rate: Moderate.

Branching characteristics: No branching, clump forming. Leaves emerge directly from base of plant.

Number of clumps per plant: Average: 7.

Number of leaves per clump: Approximately 2 or 3.

Number of leaves per plant: Approximately 17.

Age of plant described: Approximately 24 months.

FOLIAGE

Leaf:

*Arrangement*.—Equitant.

*Average length*(*excluding petiole*).—Approximately 15.7 cm.

*Average width*.—Approximately 8.1 cm.

*Shape of blade*.—Ovate.

*Aspect*.—Leaves in an average angle of 50° to horizontal (=0°).

*Apex*.—Mucronate.

*Base*.—Obtuse to cordate.

*Margin*.—Entire, undulate.

*Aspect*.—Undulating, with undulation much stronger along margin.

*Texture of top surface*.—Glabrous, very slightly glossy.

*Texture of bottom surface*.—Glabrous, very slightly glossy.

*Color*.—Young foliage upper side: Green; near RHS 143A, irregularly striped transparent Green-white; near RHS 157C to 157D. Young foliage under side: Green; near RHS 137C, irregularly striped transparent Green-white; near RHS 157C to 157D. Mature foliage upper side: Green; near RHS 137A to 137B, irregularly striped transparent White; near RHS 155C. Mature foliage under side: Green; near RHS 137B, irregularly striped transparent White; near RHS 155C.

Venation:

*Type*.—Pinnate.

*Venation coloration upper side*.—Green; near RHS 143B to 143C.

*Venation coloration under side*.—Green; near RHS 143C.

Petiole:

*Length*.—Approximately 19.9 cm.

*Width*.—At geniculum: No geniculum visible approximate width at distal end of petiole: 0.7 cm. Above clump: Approximately 1.1 cm.

*Color*.—Green to yellow-green; in between near RHS 143C and 144B.

*Strength*.—Moderate.

*General characteristics*.—Rounded with one shallow rib lengthways, smooth, slightly glossy.

Wing:

*Length*.—Approximately 7.7 cm.

*Width*.—Approximately 0.7 cm.

*Color*.—Yellow-green; near RHS 145B to 145C.

INFLORESCENCE

*Arrangement*.—Individual inflorescences grow from the centre of each clump.

*Flowering habit*.—Once a year, from late spring into summer. Quantity of spathes per plant: On average: 2 fully open spathes in good condition.

*Natural flowering season*.—Once a year, from late spring into summer.

*Time to flowering*.—Approximately 8 months from propagation.

*Fragrance*.—Not present.

*Self-cleaning or persistent*.—Persistent.

*Flower longevity*.—Flowers stay in good condition approximately 2 to 3 weeks on the plant.

Spathe:

*Aspect*.—Upright, straight on top of peduncle.

*Length*.—Approximately 9.5 cm.

*Width*.—Approximately 4.8 cm.

*Shape*.—Broad ovate to near orbicular, base folded around spadix.

*Margin*.—Entire, undulate.

*Apex*.—Mucronate.

*Base*.—Broad cuneate, circular (folded around spadix).

*Color*.—Front when opening: Yellow; near RHS 10C, margins and top Orange-red; near RHS N34A. Back when opening: Yellow; near RHS 12C, strongly tinged Red; near RHS 47A to 47C. Front when mature: Orange-red; near RHS N34A, tinged Orange near the top; near RHS 26A and 26B. Back when mature: Orange-red to greyed-red; in between near RHS N34A and 181A, tinged yellow-green towards the margin; near RHS 153B to 153D. Fading to: Orange-red to greyed-red; in between near RHS N34A and 181A.

Spadix:

*Shape*.—Columnar.

*Tip*.—Obtuse.

*Base*.—Obtuse.

*Length*.—Approximately 3.4 cm.

*Width*.—Approximately 0.8 cm.

*Diameter*.—Approximately 0.8 cm.

*Color*.—When opening: Lower 30% (female flowers) yellow-green; near RHS 154D, upper 70% (male flowers) yellow-orange; near RHS 15A.

*Mature*.—Near R.H.S. Lower 30% (female flowers) yellow-green; near RHS 150B, upper 70% (male flowers) yellow-orange; near RHS 22A.

*Spadix flower arrangement*.—Approximately 36 female flowers (consisting of a single style and ovary) approximately 400 male flowers (consisting of anthers only).

*Spadix flower diameter*.—Female flowers (consisting of a single style and ovary) Approximately 0.25 cm, male flowers (consisting of anthers only) approximately 0.1 cm.

*Spadix flower depth*.—Female flowers (consisting of a single style and ovary) Approximately 0.2 cm, male flowers (consisting of anthers only) approximately 0.75 cm.

Peduncle:

*Length*.—Approximately 30.6 cm.

*Diameter*.—Approximately 0.8 cm.

*Color*.—Yellow-green; near RHS 145A.

*Strength*.—Moderate.

REPRODUCTIVE ORGANS

*Anther color*.—Near RHS Yellow-orange 15A.

*Pollen color*.—Near RHS Yellow 11D.

*Stigma color*.—Near RHS Yellow-Orange 11A.

*Ovary color*.—Near RHS Yellow-green 150B.

OTHER CHARACTERISTICS

Disease resistance: Similar to other *Zantedeschia* varieties.

Drought tolerance and temperature tolerance: The new cultivar is a typical *Zantedeschia*, tolerant of temperatures approximately 10° to 26° C. Dought resistance similar to other *Zantedeschia* varieties.

Fruit/seed production: Not observed.

What is claimed is:

1. A new and distinct cultivar of *Zantedeschia* plant named 'CAPTAIN ODEON' as herein illustrated and described.

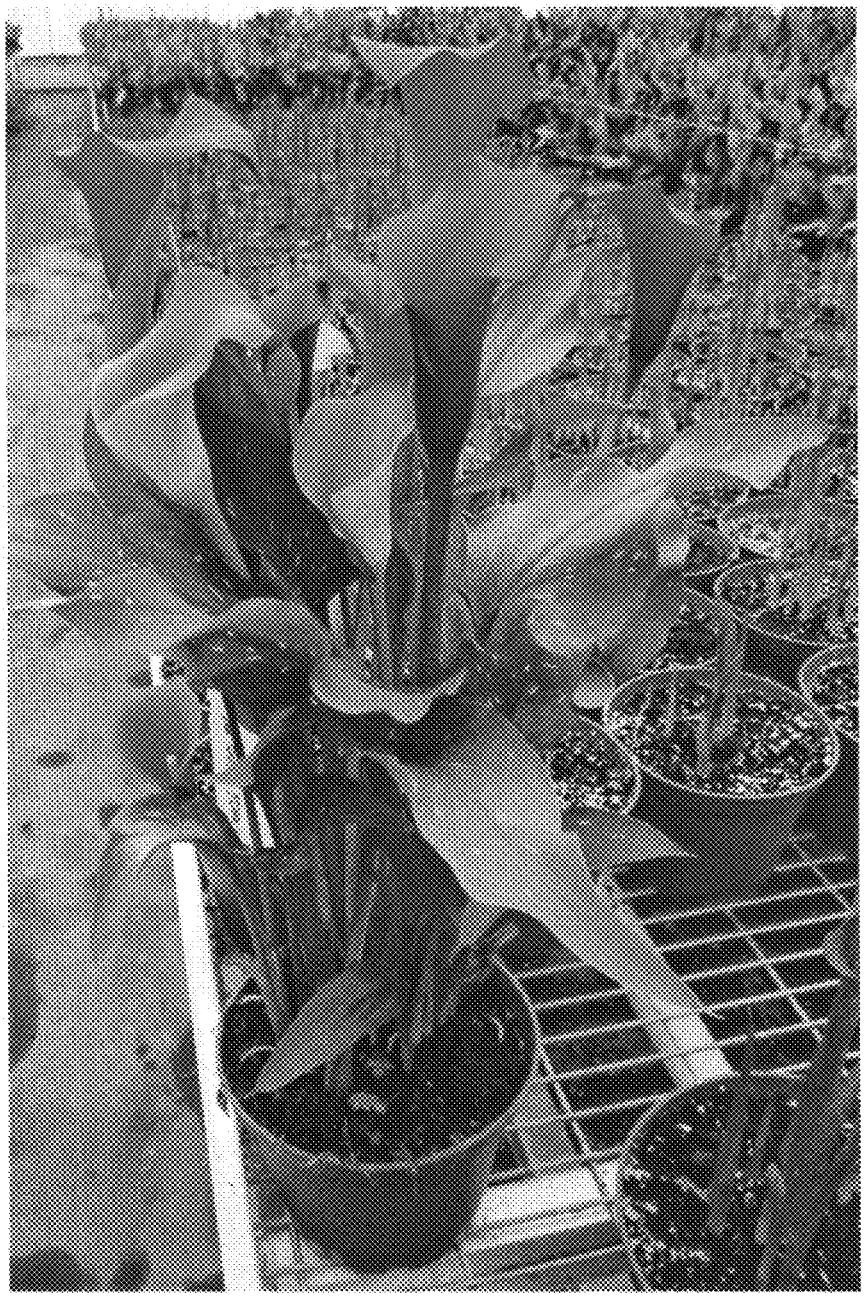

* * * * *